(12) United States Patent  (10) Patent No.: US 8,906,310 B2
Bonecker  (45) Date of Patent: Dec. 9, 2014

(54) TEST SET FOR A PHOTOMETRIC MEASURING DEVICE AND PHOTOMETRIC MEASURING METHOD FOR A SAMPLE LIQUID

(76) Inventor: Gerhard Bonecker, Baar (CH)

( * ) Notice: Subject to any disclaimer, the term of this patent is extended or adjusted under 35 U.S.C. 154(b) by 355 days.

(21) Appl. No.: 13/503,287

(22) PCT Filed: Aug. 20, 2010

(86) PCT No.: PCT/EP2010/062163
§ 371 (c)(1),
(2), (4) Date: Apr. 20, 2012

(87) PCT Pub. No.: WO2011/047902
PCT Pub. Date: Apr. 28, 2011

(65) Prior Publication Data
US 2012/0214251 A1  Aug. 23, 2012

(30) Foreign Application Priority Data
Oct. 22, 2009 (AT) ................. A 1661/2009

(51) Int. Cl.
G01N 21/00 (2006.01)
B01F 13/00 (2006.01)
B01F 13/08 (2006.01)
B01F 13/02 (2006.01)
B01L 3/00 (2006.01)
A61B 10/00 (2006.01)

(52) U.S. Cl.
CPC ............ B01F 13/002 (2013.01); B01F 13/005 (2013.01); B01F 13/0052 (2013.01); B01F 13/0818 (2013.01); B01F 13/0087 (2013.01); B01F 13/0205 (2013.01); B01F 13/0206 (2013.01); B01F 13/0224 (2013.01); B01L 3/502 (2013.01); A61B 10/0096 (2013.01); B01L 3/50825 (2013.01); B01L 3/545 (2013.01); B01L 2200/0689 (2013.01); B01L 2200/148 (2013.01); B01L 2300/022 (2013.01); B01L 2300/042 (2013.01); B01L 2300/043 (2013.01); B01L 2300/047 (2013.01); B01L 2300/048 (2013.01); B01L 2300/0832 (2013.01); B01L 2300/0838 (2013.01); B01L 2400/0406 (2013.01); B01L 2400/0478 (2013.01)
USPC ................. 422/82.05; 137/561 R; 436/164

(58) Field of Classification Search
None
See application file for complete search history.

(56) References Cited

U.S. PATENT DOCUMENTS

| 7,030,403 | B2 | 4/2006 | Feldsine et al. |
| 2008/0260581 | A1 | 10/2008 | Rosman et al. |
| 2009/0155923 | A1 | 6/2009 | Bonecker |

FOREIGN PATENT DOCUMENTS

| DE | 2441724 | 4/1975 |
| WO | 9931218 | 6/1999 |

*Primary Examiner* — Robert Xu
(74) *Attorney, Agent, or Firm* — Dykema Gossett PLLC

(57) ABSTRACT

A test set for a photometric measuring device includes a mixing container which receives a first fluid in its interior and a closing element which is removable from its filling opening, and a dosing container which contains a second fluid in a sealed hollow chamber, with the hollow chamber being sealed on one side by a displaceable sealing plunger and on the opposite side by a movable plug, and with the dosing container being insertable in a sealing manner into the filling opening of the mixing container. For the purpose of simplifying the input of the sample, the dosing container includes an integrated sample-taking device which, after the insertion of the dosing container in the filling opening of the mixing container, is in contact with the first fluid present in the mixing container.

6 Claims, 3 Drawing Sheets

TEST SET FOR A PHOTOMETRIC MEASURING DEVICE AND PHOTOMETRIC MEASURING METHOD FOR A SAMPLE LIQUID

BACKGROUND OF THE INVENTION

The invention relates to a test set for a photometric measuring device, consisting of a mixing container which receives a first fluid in its interior and a closing element which is removable from its filling opening, and a dosing container which contains a second fluid in a sealed hollow chamber, with the dosing container being insertable in a sealing manner into the filling opening of the mixing container, with the second fluid being conveyed into the interior of the mixing container by pressing a sealing plunger of the dosing container and being mixed with the same. The invention further relates to a photometric measuring method for a sample fluid which is mixed with a first and second fluid.

In many medical tests, the sample to be measured needs to be brought into contact at first with a first fluid in order to condition the sample, prepare the same for the measurement or initiate a first chemical or biological reaction. In a second step, the second fluid is added in order to transfer the analyte of the sample to be determined to a state suitable for photometric measurement or to initiate a second chemical or biological reaction. For example, in a so-called CRP measurement (C-reactive protein) which is used for distinguishing viral or bacterial inflammations, a blood sample is mixed with a lysis reagent and thereafter a latex reagent is added and mixed, with the chemical reaction being measured with the help of a photometer.

A test set of the kind mentioned above is known for example from WO 2007/053870 A2. The test set comprises a mixing container and a dosing container that can be inserted into the mixing container. The mixing container is equipped with a closing element which can be removed from a filling opening and contains a first fluid, with the dosing container being insertable into the filling opening of the mixing container after the removal of the closing element and the addition of the sample fluid to the first fluid. The dosing container contains a second fluid in a sealed hollow chamber, with the hollow chamber being sealed on the one side by a sealing plunger on the one side and by a movable plug on the other side, which after pressurizing the sealing plunger conveys the second fluid together with the movable plug into the interior of the mixing container. After the mixture of the sample with the first fluid and the second fluid, the mixing container is used in a photometric analyzer, whereupon the sample ingredients are photometrically measured. The known methods are susceptible to errors because precise sample quantities need to be supplied which are precisely required for the respective test set and the respective medical test.

A sample-taking and measuring element is known from WO 2005/071388 A1 which consists of several cylindrical compartments which are inserted into each other in an axially displaceable way, with their inside spaces being sealed in the initial position by a penetrable membrane. Two of the elements contain reagents and a sample can be introduced into the third element by a swab. The compartments are slid into each other by exerting pressure on the two outer elements, as a result of which the membranes tear at the connecting points and simultaneously the two reagent fluids are mixed with the sample. Analysis occurs either by optical inspection or by using a measuring device.

DE 24 41 724 A1 describes an analytic cartridge for photo-spectrometric measurements, comprising a first container for receiving a first fluid, with the container being sealed at first by a closing element. After the removal of the closing element, the sample to be analyzed is placed in the container and a container insert is then placed on the same which comprises a reagent fluid in an auxiliary chamber. The auxiliary chamber is provided with a cylindrical tappet which in the initial position protrudes beyond the container insert and which, when pressed down, tears open a membrane of the auxiliary chamber with the help of a cutting edge on the front side and thus releases the second fluid from the auxiliary chamber into the container with the first fluid. Once the fluids have dissolved and are mixed completely, the container is heated in the manner required for the analytic method and the sample is measured in a photometric way.

It is the object of the invention to provide a photometric measuring method for a sample fluid which offers simplest possible handling, with a improved test set being used with which errors in the precise sample dosing is to be substantially prevented. In particular, precise dosing of the sample fluid shall be enabled.

SUMMARY OF THE INVENTION

This object is achieved in accordance with the invention in such a way that the dosing container comprises an integrated sample-taking device which after the insertion of the dosing container in the filling opening of the mixing container is in contact with the first fluid present in the mixing container.

It is especially provided in accordance with the invention that the sample-taking device comprises a capillary which is open on both sides, the volume of which preferably lies between 5 µl and 50 µl.

By using an integrated sample-taking system with a capillary (end-to-end capillary) which is open on both sides, the test set will become substantially more user-friendly for the user. The capillary will automatically fill after sample contact with the volume of between 5 µl and 25 µl for example which is predetermined by the inner diameter and the length of the capillary, so that the user does not have to perform any separate pipetting steps. The user merely needs to touch the surface of the sample fluid with the end of the capillary tube, with the tube filling up by the capillary effect and with precisely the sample volume predetermined for the respective sample measurement being sucked in.

The measuring method in accordance with the invention in which the first fluid is present in an initially sealed mixing container and the second fluid in a dosing container whose hollow space is sealed by a plug is characterized by the following steps:

- Taking the sample fluid by means of a sample-taking device fixed to the dosing container;
- opening of the mixing container;
- inserting the dosing container into the mixing container, with the sample fluid present in the sample-taking device being introduced into the mixing container;
- mixing of the first fluid with the sample fluid by shaking the mixing container;
- introducing the second fluid from the dosing container into the mixing container, with pressure being exerted on the second fluid and with the same being discharged together with the plug into the first fluid;
- mixing of the first fluid, the sample fluid and the second fluid;
- photometric measurement of the chemical reaction in an analyzer, and calculating the concentration of at least one sample ingredient.

BRIEF DESCRIPTION OF THE DRAWINGS

The invention will be explained below in greater detail by reference to the drawings, wherein.

DETAILED DESCRIPTION OF THE DEPICTED EMBODIMENT

Figure 2:
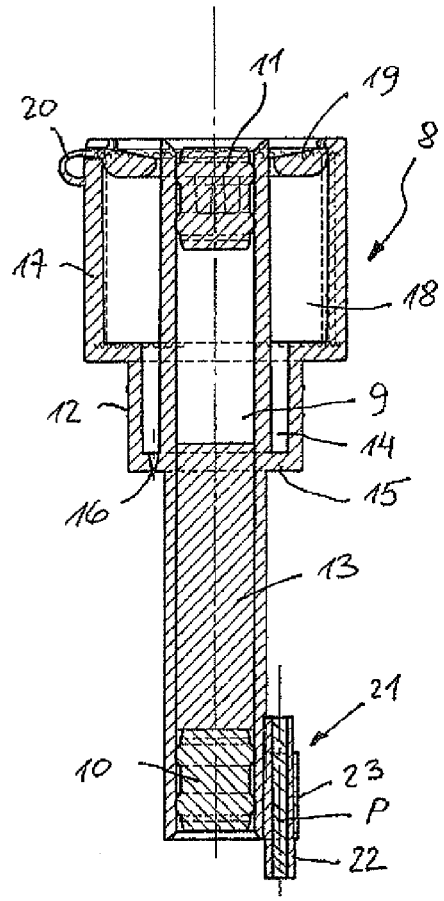
FIG. 2 shows the mixing container of the test set in accordance with the invention in a sectional view.
Figure 1:
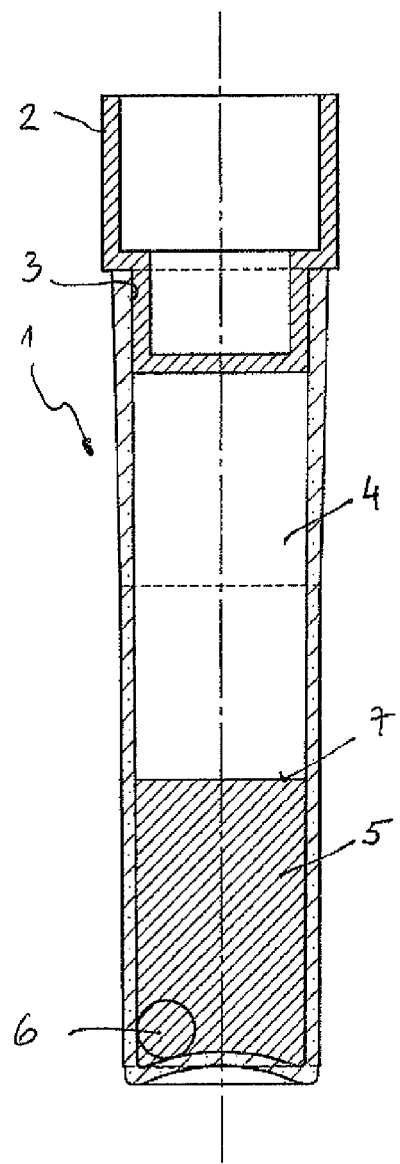
FIG. 1 shows the mixing container of the test set in accordance with the invention in a sectional view.
Figure 3:
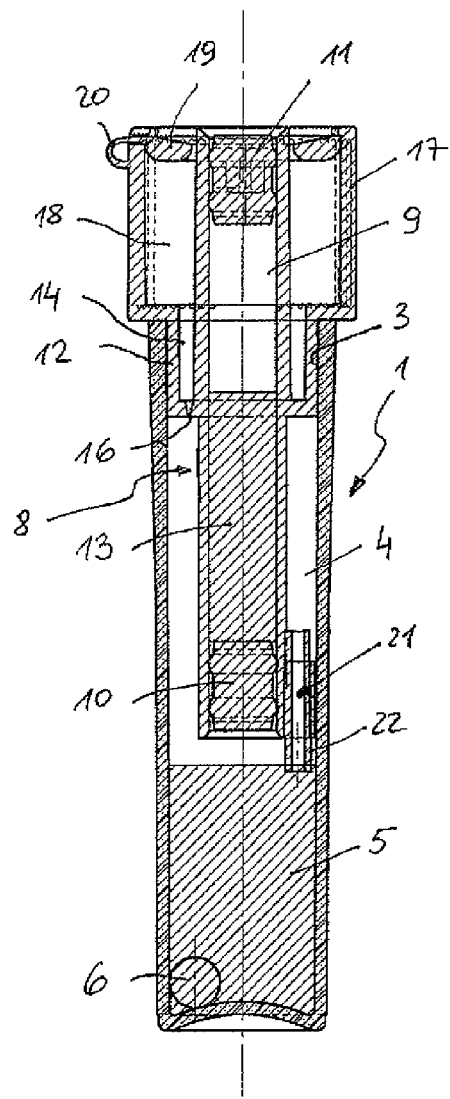
FIG. 3 shows the dosing container according to FIG. 2 inserted in the mixing container in a first measuring position.

The test set shown in FIGS. 1 to 5 is used in a photometric measuring device or analyzer as shown in WO 2007/053870 A2 for example. The mixing container 1 of the test set comprises a closing element 2 such as a removable plastic plug which seals the filling opening 3. A first fluid 5 is disposed in the interior 4 of the mixing container 1 as well as a magnetic stirrer or a steel ball 6. An air space is disposed above the first fluid 5, with the surface of the fluid being indicated with reference numeral 7.

The dosing container 8 which can be inserted into the mixing container 1 comprises a cylindrical hollow space 9 which is sealed at one end (on the outlet side) by a plug 10. An axially displaceable sealing plunger 11 is disposed on the opposite side in the hollow space 9, which sealing plunger is either displaced manually in a downward direction, or on which an actuating stamp of an analyzer (not shown) can exert a pressure.

The sample-taking device 21 comprises a capillary 22 which is open on both sides, the volume of which is adjusted precisely to the requirements of the respective measuring method and preferably lies between 5 µl and 50 µl. The user merely needs to bring the capillary 22 into contact with the surface of the sample fluid to be measured, which capillary is preferably fastened to the side of the dosing container 8 and protrudes beyond the end region of the dosing container 8, whereupon the sample fluid P is automatically sucked into the sample-taking device 21 by means of the capillary effect and in the quantity predetermined by the volume of the capillary. FIG. 2 shows the capillary 22 which is filled with the sample fluid P.

In accordance with the invention, the capillary 22 can be produced by coextrusion and can be formed on the dosing container 8. A plastic material can be used which is optimal for the capillary and which differs from the plastic material of the dosing container.

In accordance with one variant, the capillary 22 can be held in a receptacle 23 formed on the end region of the dosing container 8.

The dosing container 8 comprises a cylindrical sealing area 12 for the sealing application in the mixing container 1, which sealing area is formed on the dosing container 8 with an annular flange 14 and forms an annular space 15, with at least one venting opening 16 being arranged in the annular flange 14. When the dosing container 8 is inserted into the mixing container 1 (see FIG. 3), the air displaced by the dosing container 8 from the interior 4 can be released through the gas-permeable, approximately droplet-tight venting opening 16. The sample fluid can now be mixed with the first fluid 5 by shaking the mixing container 1.

In accordance with the invention, a cylindrical or ergonomically optimized handle element 17 is formed adjacent to the cylindrical sealing area 12 of the dosing container 8, which handle element delimits an annular space 18 and can be sealed to the outside by an annular splash protection element 19. The outlet of fluid from the test set can effectively be prevented by the splash protection element 19.

After the mixing of the first fluid 5 with the sample fluid P, a photometric calibrating measurement (in the first measuring position of the set) can be performed in the analyzer.

Figure 4:
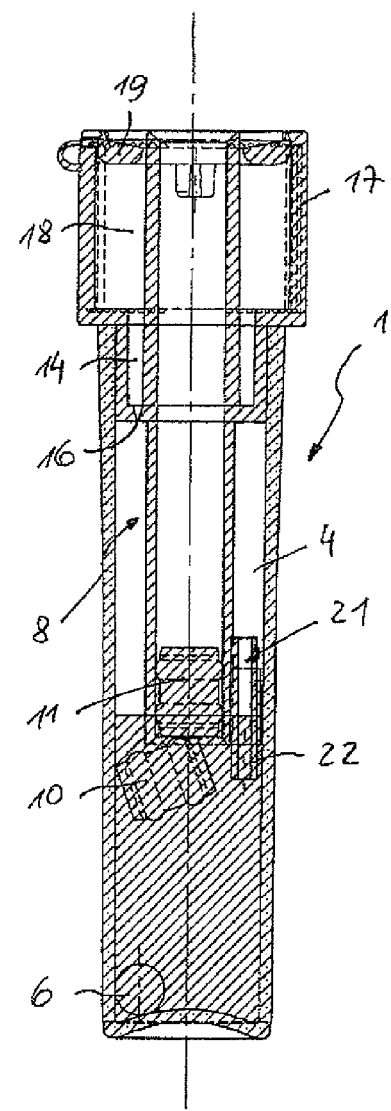
FIG. 4 shows the dosing container according to FIG. 2 inserted in the mixing container in a second measuring position.
Figure 5:
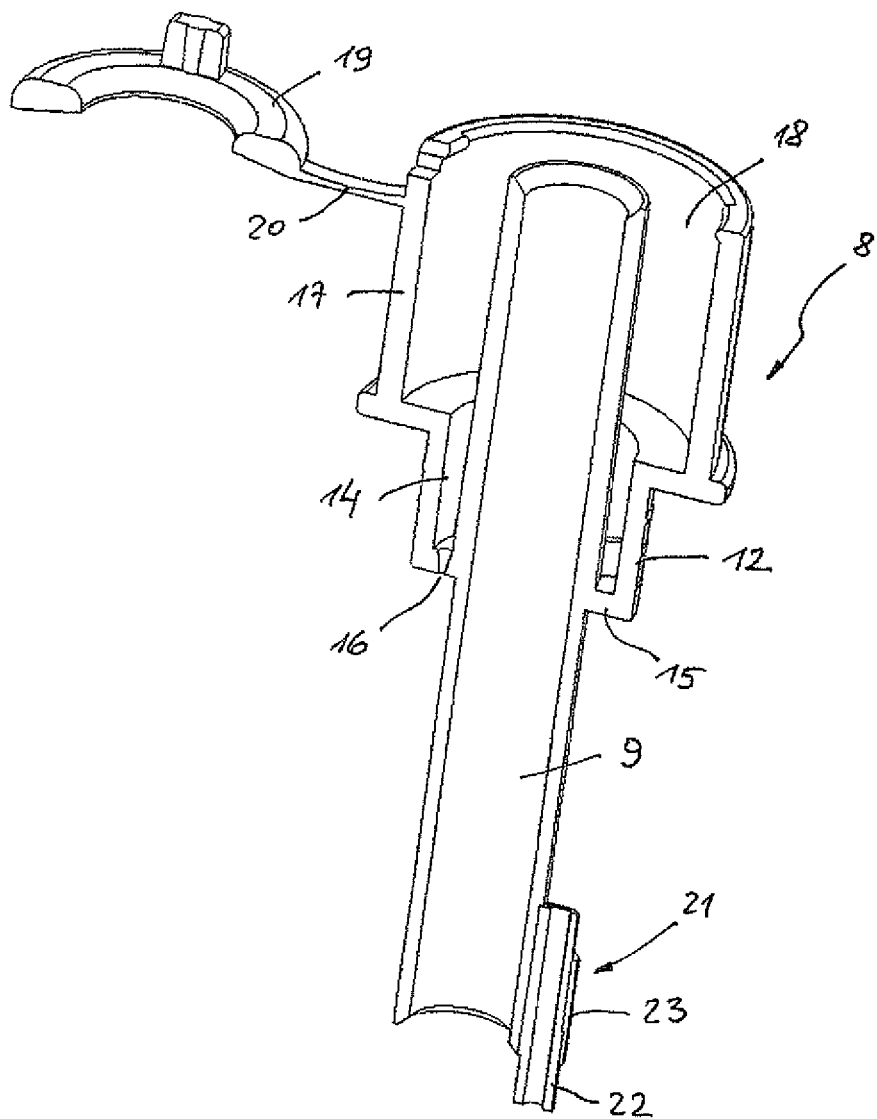
FIG. 5 shows a three-dimensional illustration of the dosing container in a sectional view according to FIG. 2.

The second fluid is thereupon transferred according to FIG. 4 with the help of the plunger 11 from the dosing container 8 into the interior 4 of the mixing container 1, with the plug 10 exiting the dosing container 8 and floating in the mixing container 1. A magnetic stirrer of the analyzer which acts upon the steel ball 6 can further be activated, by means of which the mixture is homogenized and is then photometrically measured (second measuring position of the set) as explained in WO 2007/053380 A2 for example.

First Example

INR/PT Test

INR determination is a test for the purpose of determining how fast the blood of the human will coagulate. The normal value of INR is 1; at an INR value of 4 for example blood will coagulate four times slower. A high INR value therefore means that blood coagulation does not work as well as in a healthy person.

Whole blood taken directly from the patient is used for examination and is introduced into the capillary, or blood plasma from sample tubes which are laced with citrate.

The first INR reagent is disposed in the mixing container 1 and the second INR reagent is in the dosing container 8.

Test procedure of the INR test:
  A blood sample is brought into contact with the capillary 22 of the dosing container 8 and a defined sample volume is sucked in;
  Mixing container 1 is sealed at first with closing element 2 and filled with lysis reagent (80 µl-150 µl);
  Closing element 2 is removed, dosing container (containing latex reagent) is inserted together with the integrated capillary into the mixing container 1 in a sealing manner;
  Mixing container 1 and dosing container 8 are shaken in the closed state until sample fluid exits from the end-to-end capillary 22 into the mixing container 1;
  Mixing container 1 and dosing container 8 are inserted into a measuring device (e.g. analyzer from WO 2007/053380 A2);
  Test identification by the measuring device (by RFID chip in the packaging or on the mixing container);
  Lysis reagent and sample liquid are mixed by means of a magnetic stirrer of the measuring device (optional);
  The calibration value is measured (optional);
  Latex reagent (50 µl-200 µl) is dosed and added with the help of a stamp of the measuring device or manually by pressure on the sealing plunger 11;
  Lysis reagent, sample fluid and latex reagent are mixed with the help of the magnetic stirrer;
  The chemical reaction is measured with the help of the photometer;

The coagulation time is determined.

The measuring range of the photometric measuring device is INR 0.5-INR 5 for example.

Second Example

HCY Test

From a chemical standpoint, homocysteine (HCY) belongs to the group of the so-called amino acids. In the body, homocysteine is formed from methionine, another amino acid, which is supplied with food. Homocysteine is normally degraded very rapidly, with vitamin B6 (pyridoxine), vitamin B12 (cobalamin) and folic acid being required.

Homocysteine was identified as a separate risk factor for atherosclerotic or thromboembolic events (peripheral arterial occlusive vascular disease, stroke, coronary heart disease (angina, cardiac infarction), occlusive changes to the carotid artery). In a number of further diseases such as old-age dementia, development of defects in the neural canal (spina bifida) of the child in the womb and anemia, a connection with increased homocysteine levels was established.

The first HCY reagent is located in the mixing container 1. The second HCY reagent is located in the dosing container 8. The test sequence occurs as in example 1.

Target range for homocysteine is below 10 μmol/l in the serum.

Third Example

CRP Test

A measuring sequence of a CRP test (C-reactive protein, which is used mainly for differing between viral and bacterial inflammation) is illustrated as a third example.

A lysis reagent (1000 μl) is disposed as the first fluid in the mixing container 1.5 μl of whole blood are sucked in with the capillary 22 of the dosing container 8. The dosing container 8 contains a latex reagent (250 μl). The lysis reagent is mixed with the whole blood sample first and a calibration value is measured. Thereafter the latex reagent is added in a dosed manner and the concentration value is determined photometrically after the chemical reaction. The test sequence occurs as in example 1.

The measuring range of the photometric measuring device is at 0.2 mg/dl to 6 mg/dl for example.

The following advantages of the test set in accordance with the invention can be mentioned especially:

The user does not have to perform any separate pipetting steps.

High precision of the obtained sample volume.

A lot of time saved in taking the sample.

Reduction in costs by avoidance of separate sample-taking devices.

The invention claimed is:

1. A test set for a photometric measuring device, comprising
   a mixing container which defines a filling opening and which receives a first fluid in an interior thereof, and a closing element which is removable from the filling opening; and
   a dosing container which is insertable in a sealing manner in the filling opening of the mixing container and which contains a second fluid in a sealed hollow chamber which is sealed on one side by a displaceable sealing plunger and on an opposite side by a movable plug, wherein the dosing container comprises an integrated sample-taking device which, after the insertion of the dosing container in the filling opening of the mixing container, contacts the first fluid present in the mixing container, wherein the sample-taking device comprises a capillary which is open on both sides and whose volume is preferably between 5 μl and 50 μl.

2. The test set according to claim 1, wherein the capillary is held in a receptacle formed in the end region of the dosing container.

3. The test set according to claim 1, wherein the capillary is produced by coextrusion and is formed on the dosing container.

4. The test set according to claim 3, wherein the capillary is fastened laterally to the dosing container and protrudes beyond the end region of the dosing container.

5. The test set according to claim 4, wherein the dosing container comprises a cylindrical sealing area for application in the mixing container, which sealing area is formed on the dosing container with an annular flange and forms an annular space, with at least one venting opening in the annular flange.

6. The test set according to claim 5, wherein a handle element which is cylindrically or ergometrically optimized is formed adjacent to the cylindrical sealing area, which handle element delimits an annular space and can be sealed to the outside by an annular splash protection element.

\* \* \* \* \*